(12) United States Patent
Schwarz et al.

(10) Patent No.: US 10,195,453 B2
(45) Date of Patent: Feb. 5, 2019

(54) DEVICE INCLUDING RF SOURCE OF ENERGY AND VACUUM SYSTEM

(71) Applicant: BTL Holdings Limited, Nicosia (CY)

(72) Inventors: Tomáš Schwarz, Prague (CZ); Ondrej Pribula, Prague (CZ); František Lang, Volyně (CZ)

(73) Assignee: BTL Holdings Limited, Nicosia (CY)

( * ) Notice: Subject to any disclaimer, the term of this patent is extended or adjusted under 35 U.S.C. 154(b) by 0 days.

(21) Appl. No.: 15/584,747

(22) Filed: May 2, 2017

(65) Prior Publication Data

US 2017/0348539 A1    Dec. 7, 2017

Related U.S. Application Data

(60) Provisional application No. 62/333,666, filed on May 9, 2016, provisional application No. 62/331,060, filed on May 3, 2016, provisional application No. 62/331,088, filed on May 3, 2016, provisional application No. 62/331,072, filed on May 3, 2016, provisional application No. 62/351,156, filed on Jun. 16, 2016, provisional application No. 62/358,417, filed on Jul. 5, 2016, provisional application No. 62/375,796, filed on Aug. 16, 2016, provisional application No. 62/340,398, filed on May 23, 2016.

(51) Int. Cl.
*A61N 1/40* (2006.01)
*A61N 1/32* (2006.01)
*A61N 1/04* (2006.01)

(52) U.S. Cl.
CPC .......... *A61N 1/403* (2013.01); *A61N 1/0404* (2013.01); *A61N 1/048* (2013.01); *A61N 1/0472* (2013.01); *A61N 1/328* (2013.01)

(58) Field of Classification Search
CPC ................................ A61N 1/328; A61N 1/403
See application file for complete search history.

(56) References Cited

U.S. PATENT DOCUMENTS

| | | | |
|---|---|---|---|
| 6,273,884 B1 * | 8/2001 | Altshuler | A61B 18/203 606/2 |
| 9,867,996 B2 * | 1/2018 | Zarsky | A61N 1/403 |
| 2013/0123764 A1 * | 5/2013 | Zarsky | A61B 18/18 606/13 |
| 2013/0123765 A1 * | 5/2013 | Zarsky | A61N 1/40 606/13 |
| 2013/0238061 A1 | 9/2013 | Edoute et al. | |
| 2014/0249609 A1 * | 9/2014 | Zarsky | A61N 1/40 607/102 |
| 2016/0045755 A1 * | 2/2016 | Chun | A61F 7/10 607/102 |

* cited by examiner

*Primary Examiner* — Kaityln Smith
(74) *Attorney, Agent, or Firm* — Kenneth H. Ohriner; Perkins Coie LLP (57) ABSTRACT

A method of soft tissue treatment of a patient includes placing an applicator onto a surface of the soft tissue, with the applicator including an electrode and a dielectric material vacuum cup. The soft tissue is heated via the electrode. Vacuum is applied to the vacuum cup. The electrode may be at least partially covered by a dielectric material of variable thickness.

27 Claims, 5 Drawing Sheets

DEVICE INCLUDING RF SOURCE OF ENERGY AND VACUUM SYSTEM

PRIORITY CLAIM

This Application claims priority to U.S. Provisional Patent Application Nos. 62/333,666, filed May 9, 2016; 62/331,060, filed May 3, 2016; 62/331,088, filed May 3, 2016; 62/331,072, filed May 3, 2016; 62/351,156, filed Jun. 16, 2016; 62/358,417, filed Jul. 5, 2016; 62/375,796, filed Aug. 16, 2016 and 62/340,398, filed May 23, 2016, incorporated herein by reference.

FIELD OF THE INVENTION

This invention relates to noninvasive, aesthetic, automated radio-frequency (RF) treatment devices and methods for treating soft tissue using an RF electrode and a vacuum system.

BACKGROUND OF THE INVENTION

Soft tissue includes skin, muscle, fat, connective tissue (e.g. collagen fibers), nervous tissue (e.g. neurons, motor neuron and neuromuscular junction), cartilage, veins, artery, body fluids (e.g. blood, lymph and/or other body liquids) and other soft structures.

Human skin is composed of three basic elements: the epidermis, the dermis and the hypodermis or so called sub cutis. The dermis consists of collagen, elastic tissue and reticular fibers. The hypodermis is the lowest layer (structure) of skin and contains hair follicle roots, lymphatic vessels, collagen tissue, nerves and also subcutaneous fat forming an adipose tissue.

Adipose tissue is formed by aggregation mostly of adipose cells mostly containing stored fats as triglycerides. Triglycerides are esters of three fatty acid chains and the alcohol glycerol (fat). Most adipose tissue accumulations result from fat primarily from food, when energy intake derived from food exceeds daily energy needs. This may result in an increase in fat cell size or fat cell number or both. Mature fat cells are very large, ranging up to 40 microns in diameter and containing as much as 95% lipid (fat) by volume. The subcutaneous adipose tissue layer may be thin (about 1 cm or less) in humans of slight or moderate body type. It is possible to distinguish different types of adipose tissue. Adipose tissue may mean visceral (fat) adipose tissue located adjacent to internal organs, subcutaneous adipose tissue located beneath the skin but above skeletal muscle and/or adipose tissue located between the muscle fibers.

Excess adipose tissue may be perceived as aesthetically undesirable. Excess adipose tissue may lead to health complications Dieting and exercise may result in reduction of adipose tissue and weight loss. However, the reduction in adipose tissue volume occurs rather unpredictably from all anatomical areas. This can leave the areas intended for reduction (e.g. the abdomen) largely unaffected, even after significant body weight loss. Dieting and exercise may also cause discomfort, physical and psychic stress. Various invasive and non-invasive methods have been developed to remove unwanted subcutaneous fat from specific areas of the body.

The main invasive method is surgical-assisted liposuction, where selected volumes of adipose tissue are mechanically aspirated out of the patient at desired anatomical sites of the body. However, liposuction procedures are invasive and can be painful and traumatic, with many undesirable side effects and risks. Lipodissolve is another invasive procedure involving a series of drug injections intended to dissolve and permanently remove small pockets of fat from various parts of the body. It is also known as mesotherapy, lipozap, lipotherapy or injection lipolysis. Lipodissolve has many disadvantages and risks also, to the extent that various medical associations have issued health warnings against using it.

The non-invasive methods concentrate on the acceleration of the lipolysis as the natural process of the fat reduction. This can be achieved in several ways. One of them is application of pharmaceuticals accelerating the lipolysis. However, when applied topically they tend only to affect the outermost layers of the skin, rarely penetrating to the sub dermal vascular plexus. Another method uses radio frequency or ultrasound energy focused on adipose tissue to cause cell destruction and cell death. These methods tend to damage the melanocyte in the epidermis. The hyper thermic temperatures destroy the target tissues and leave the body to remove the dead cellular and other debris. Non-invasive heating techniques have also been used. These non-invasive methods have certain disadvantages as well (e.g. inhomogeneous soft tissue heating, creating of hot spots, panniculitis etc.), and have been used with varying degrees of success.

Accordingly, there is need for improved methods and systems for subcutaneous treatments. There is also a need to improve the energy flow through the tissue of treated patient to reduce or eliminate risks of overheating of non-target soft tissue, improve homogeneity of heating desired layer of soft tissue in order to prevent hot spots. Heating of soft tissue by an external source of energy may cause other undesired effect and health complications e.g. non-controlled heating or overheating of the soft tissue that is also needed to improve.

SUMMARY OF THE INVENTION

Apparatus and methods provide RF (radio-frequency) treatment with applied negative pressure (pressure lower than atmospheric pressure).

In order to provide ideal transfer of a RF (radio-frequency) treatment energy into the soft tissue adjusting parameters of soft tissue may greatly affect the results. Parameters of the soft tissue that may be influenced are polarity, dielectric constant, specific heat capacity, coefficient of thermal diffusion and/or others) that may be provided by e.g. by increasing/decreasing temperature, body liquids flow and/or other mechanisms; in the treated soft tissue. Varying RF signal parameters to enhance RF signal penetration and/or targeting to specific soft tissue structure may also be required to achieve desired results. RF signal parameters include, for example, frequency, polarization of RF waves, ratio between magnetic and electric component of RF waves, output power, pulse intensity, pulse duration, sequence of pulses, shape of pulses, envelope of provided signal, duration of continual radiation, distance between the electrode, orientation of the electrode, surface of the electrode, shape of the electrode, shape of electromagnetic field, homogeneity of electromagnetic field, flux density of provided RF signal and/or others.

Knowing the dielectric constant (mainly its complex part) of specific soft tissue structure may be important when providing treatment using an electromagnetic field e.g. RF energy. The dielectric constant behaves as a parameter with real and imaginary parts that depend on several physical quantities. The dielectric constant of specific soft tissue structure may depend on the frequency of the RF energy source, the ratio between electric and magnetic components of the RF waves, the direction of spreading of the RF wave, the temperature of the environment where RF wave spreading occurs, distance and/or other factors.

Tissue with a low complex dielectric constant is heated more quickly than tissue with a high complex dielectric constant during capacitive RF energy transfer in frequency ranges up to 0.5 MHz or more preferably up to 10 MHz. For example, bone tissue and adipose tissue have a low dielectric constant in comparison to muscle. Absorbed power of adipose tissue ($P_a$) and muscle tissue ($P_m$) is different. The ratio (Pa/Pm) is large, as a consequence of relatively small conductivity ratio ($\delta a/\delta m$) and dominantly a large permittivity ratio ($|\varepsilon_m*|^2/|\varepsilon_a*|^2$), such that a relatively large absorption occurs in the adipose tissue.

Increasing of a temperature in the soft tissue may have other positive effects. Hyperthermia may be used in order to vary physical parameters of the soft tissue, to improve regeneration of injured muscles, cartilage, other soft tissue deficiencies, to improve blood flow, lymph flow, remove degeneration caused by aging, or excrescent of adipose.

The apparatus may provide heating of the soft tissue by thermal diffusion from an applicator to the patient's body and/or heat by delivered one or more other treatment energy sources e.g.: the dielectric loss RF treatment energy by an RF treatment energy source.

Changing temperature of the soft tissue before, during and/or after the treatment may influence pain receptors, soft tissue laxity, dielectric properties of soft tissue, improve homogeneity of distributed energy delivered to the soft tissue by the treatment energy source (e.g. prevent hot spots), stimulate fat metabolism, prevent edge effects, and/or create temperature differences in the soft tissue. A temperature of the soft tissue target area during the treatment may be selectively adjusted with or without changing temperature of adjacent areas, in order to improve comfort and/or effectiveness of the treatment.

Various aesthetic skin and/or body treatment effects may be provided by the present methods and devices including: anti-ageing (e.g.: wrinkle reduction, skin tightening, hydrating the skin, skin rejuvenation, skin viability, removing of pigment deficiencies and/or pigmentation correction); skin disease (e.g.: rashes, lupus, fungal diseases, surface antimicrobial treatment procedure, hyperthermia, hyperaemia); soft tissue relaxation (e.g.: muscle and/or other soft tissue layers relaxation); body shaping (e.g.: fat removing, removing of unwanted soft tissue laxity, removing of cellulite, building muscle mass and strength, accelerating fat metabolism of a cells, restructuring of the connective tissue; increase in the number of fibroblasts, enhancement of fibroblast proliferation, by neocolagenesis and/or elastogenesis); and/or other soft tissue deficiencies (e.g.: by accelerating body metabolism, stimulating the lymphatic circulation), circumferential reduction influence membrane transport of a cell, a proliferation of chondrocytes in the cartilages, increase in blood perfusion, blood flow and venous return, wound healing, disinfection of the patient surface and/or relieving of a patient's body pain).

Predefined treatment therapy methods may be manually performed by an operator and/or automatically performed by controlling mechanism (e.g. control unit) or changed during the treatment based on feedback parameters, based on the treatment protocol and/or based on previous treatment or measurement. Multiple treatment energy sources may be combined to provide a synergic effect on human tissue. This improves effectivity of the treatment and/or reduces time needed for the treatment. It may also improve safety of the treatment e.g. stimulation of soft tissue by massage improves blood and lymph stimulation which in combination with an RF field provides improves removal of treated fat cells (prevention of panniculitis), improves homogeneity of delivered energy in to the soft tissue, targeting of delivered energy to the soft tissue, reduces pain during the therapy and/or a decreases the influence of edge effects and overheating of a part of the soft tissue due to enhanced body liquid circulation.

Another example of synergic effects may be utilization of plasma (e.g. non-thermal plasma), where an RF electrode may regulate plasma, help to create plasma and/or adjust some parameters of plasma. Several treatments in combination may provide better transfer of the energy to a specific layer of the soft tissue; e.g. preheating, massage of the patient skin surface to accelerate blood flow that increases the complex dielectric constant of the surface and increases penetration of such layer by RF waves.

The apparatus may operate without any operator which saves time and reduces costs of the treatment. The apparatus may automatically control parameters of treatment energy and/or other parameters of the device associated with treatment. One operator may supervise more than one treated patient. Self-operated devices may prevent mistakes during the treatment caused by human factors. A self-operated device may also have a better response to changed conditions of the treatment and/or may provide more homogenous and precise treatment which improves results and safety of the treatment. A computer may have a better response to changed conditions because it can react faster than 0.001 s, whereas human response on occurrences like moving of the patient, or structural changes in the soft tissue is at least 0.5 s. Another benefit of self-operated devices may be that the operator does not have to be as skilled as when using manual device.

The applicator may be adjacent to patient surface and it may be flexible and of arbitrary size and shape. This characteristic helps to provide optimal energy transfer from an applicator to the patient soft tissue. More perfect contact with the patient surface may decrease or prevent the edge effect backscattering of delivered energy (which may improve focusing of the delivered energy) and/or provides optimal conditions for collecting feedback information. Direct contact with the patient surface may also be used for accurate and fast regulation of patient surface temperature.

GLOSSARY

Soft tissue structure or specific soft tissue part is a part of the soft tissue that exhibits the same or nearly the same physical parameters and/or structural characteristic (e.g. water content, content and structure of collagen, protein content, stiffness etc.). Examples of different specific soft tissue structures are: collagen fibers, veins, adipose tissue, keranocites in epidermis, nerves, muscle, ratilage and/or other soft tissue structures.

Treatment protocol is a software protocol that defines treatment parameters, guides treatment process of one or more treatment energy sources and defines parameters of provided treatment energy. At least part of the treatment protocol may be preprogramed in a control unit, other controlling mechanism, or may be used from an external device (e.g.: downloaded from a network or recorded from an external device). Treatment protocol may be design, selected and/or adjusted by an operator and/or by software in a control unit, external device and/or by other controlling mechanism based on feedback information and/or previous experience. Two or more protocols may be composed together and create new one treatment protocol.

An external device is a device including hardware and software provided separately from the treatment device. An external device may be e.g.: a computer, smartphone, tablet, USB flash disc, or other equivalent device. The external device communicates with a control unit and/or may communicate with other controlling mechanisms.

A treatment energy source is a hardware part of the device that may provide treatment energy in order to provide treatment effects.

Treatment energy is energy provided to the patient's body in order to cause treatment effects. Treatment energy provided by the device may be focused or unfocused, selective or non-selective. Applied treatment energy may be: RF, light, electric current, plasma, continual and/or time varying magnetic field, acoustic wave (including ultrasound), shock wave, mechanical friction of patient's skin surface, heating, cooling, or applied pressure to the patient soft tissue.

Treatment effect is an effect caused by treatment energy in the patient's body. Treatment effect may also be influenced and/or caused by applied active substances described below. Treatment effect causes intended metabolic and/or structural changes in the patient's soft tissue and/or cells. Treatment energy may be targeted to cause treatment effect in a bone tissue. The device may provide treatment effects: wrinkle reduction, skin tightening, hydration of the skin, skin rejuvenation, skin viability, removing of pigment deficiencies, slowing of soft tissue aging process, treating of rashes, treating of lupus, treating of fungal diseases, surface antimicrobial treatment procedure, hypothermia, hyperaemia, soft tissue relaxation e.g.: muscle, sinew and/or other soft tissue layers relaxation; body shaping e.g.: adipose cell volume downsizing, adipose cell removing, removing of unwanted soft tissue laxity, removing of cellulite, building muscle mass and strength, accelerating fat metabolism of a cells, restructuring of the connective tissue; increase in the number of fibroblasts, enhancement of fibroblast proliferation, neocollagenesis and/or elastogenesis; acceleration of body metabolism, stimulation of blood and lymphatic circulation, circumferential reduction influence membrane transport of a cell, a proliferation of chondrocytes in the cartilages, increase in blood perfusion, blood flow and venous return, wound healing, restore nerve functionality, influence cell proliferation, disinfection of the patient surface and/or relieving of a patient body pain, enhancing of bone density.

Treatment parameters may be any parameters influencing the treatment of the patient. Treatment parameters mainly determine type and parameters of the treatment energy. Treatment parameters may be: value of applied pressure, switching on/off sequence of specific treatment energy source or sources, intensity of delivered treatment energy, targeting of the treatment energy, pulse duration, pulse sequence, frequency of delivered energy by treatment energy source, amount of delivered radiation, energy flux density, duration of delivered treatment energy, timing of applied treatment energies, temperature value of the soft tissue and/or part of the device, focusing parameters of delivered treatment energy as focal spot volume, depth, electric voltage on the treatment energy source, intensity of provided magnetic field and/or other parameters, distance e.g. between treatment energy source and patient's skin surface (epidermis) and/or other parameters.

A shape adaptive material adapts its shape and volume as influenced by external forces.

An elastic material adapts its shape but not volume. The elastic material may stretch or deform to adapt to external forces.

Target area/tissue is part of the soft tissue targeted by focused or unfocused treatment energy to provide treatment effect.

Discomfort temperature is the temperature of at least part of the patient's soft tissue that becomes painful and/or highly uncomfortable according the patient's subjective feeling.

Comfortable temperature is the temperature of at least part of the patient's soft tissue that is tolerable for the patient according subjective patient's filling, treatment protocol and/or feedback information from specific sensors.

Bolus is a special embodiment of dielectric material with a cavity inside located between patient surface and the treatment source of energy. The cavity of the bolus may be filled with fluid that may be any type of gas, liquid, gel, suspension and/or mixture. Fluid may also flow through the bolus and may regulate its temperature and/or dielectric parameters.

RF electrode or electrode in this text has the same meaning. RF electrode is treatment energy source that may provide RF treatment energy or electrotherapy.

Contact part of the applicator is part of the applicator located below the treatment energy source which is in direct contact with the patient's skin surface. Contact part of the applicator may be dielectric material (e.g. see part 401a FIG. 4) or surface of the treatment energy source. Vacuum edge is not considered as contact part of the applicator.

BRIEF DESCRIPTION OF THE DRAWINGS

FIGS. 9A-9C are views of a magnetic connector for transferring high frequency signals or data.

DETAILED DESCRIPTION OF THE INVENTION

The device and method provide treatment of soft tissue by applying at least one treatment energy source. Treatment may be based on selective capacitive and/or targeted inductive heating of the target soft tissue. Target tissue may be adipose tissue, collagen fibers and/or other part of the soft tissue where treatment energy is provided in a targeted manner in order to provide a treatment effect. Treatment may also restore and accelerate cell metabolism, improve lymphatic circulation, blood circulation and/or blood supply of dermis.

The device may be used to remove and/or reduce: wrinkles, spider veins, volume of fat cells, number of fat cells, cellulite, redness of skin, pigment inhomogeneity, lupus symptoms, scars, acne and/or other body imperfections.

The device may also be used for rejuvenate skin, improve skin elasticity, skin hydration, circumferential reduction, body contouring and/or other treatment effect described in glossary.

The method and device may provide one or more treatment energy sources in order to provide treatment to the patient e.g.: vacuum (constant or variable pressure value under the applicator), mechanical wave energy (ultrasound wave energy, shock wave energy), light energy, plasma, thermal energy, electric current, magnetic field and/or preferably radio-frequency treatment energy (RF). Different treatment energy produced by treatment energy sources and different treatment effect may be used individually and/or may be combined. Different treatment energy may be combined in one or more treatment energy sources in one or more applicators. Such an example may be an RF electrode as a first treatment energy source and piezo element as a second treatment energy source wherein both treatment energy sources may be placed in one applicator or separate applicators. The device may treat any part of the patient body e.g. face, double chin, thighs, saddlebags, buttocks, abdomen, region of bra fat, arm, etc. The specific treatment energy as electric and/or magnetic muscle stimulation may be targeted to at least part of specific muscle group to stimulate at least part of one muscle fiber. Muscle groups may be major muscle group e.g.: upper back, infraspinatus, deltoids, biceps, triceps, forearms, chest muscle, middle back, lower back, side abs, rectus abdominis, gluteus maximus, hamstring group, quadriceps, tibialis anterior, calf; and/or deep muscle e.g.: pelvic floor muscles, psoas major muscle.

Figure 1:
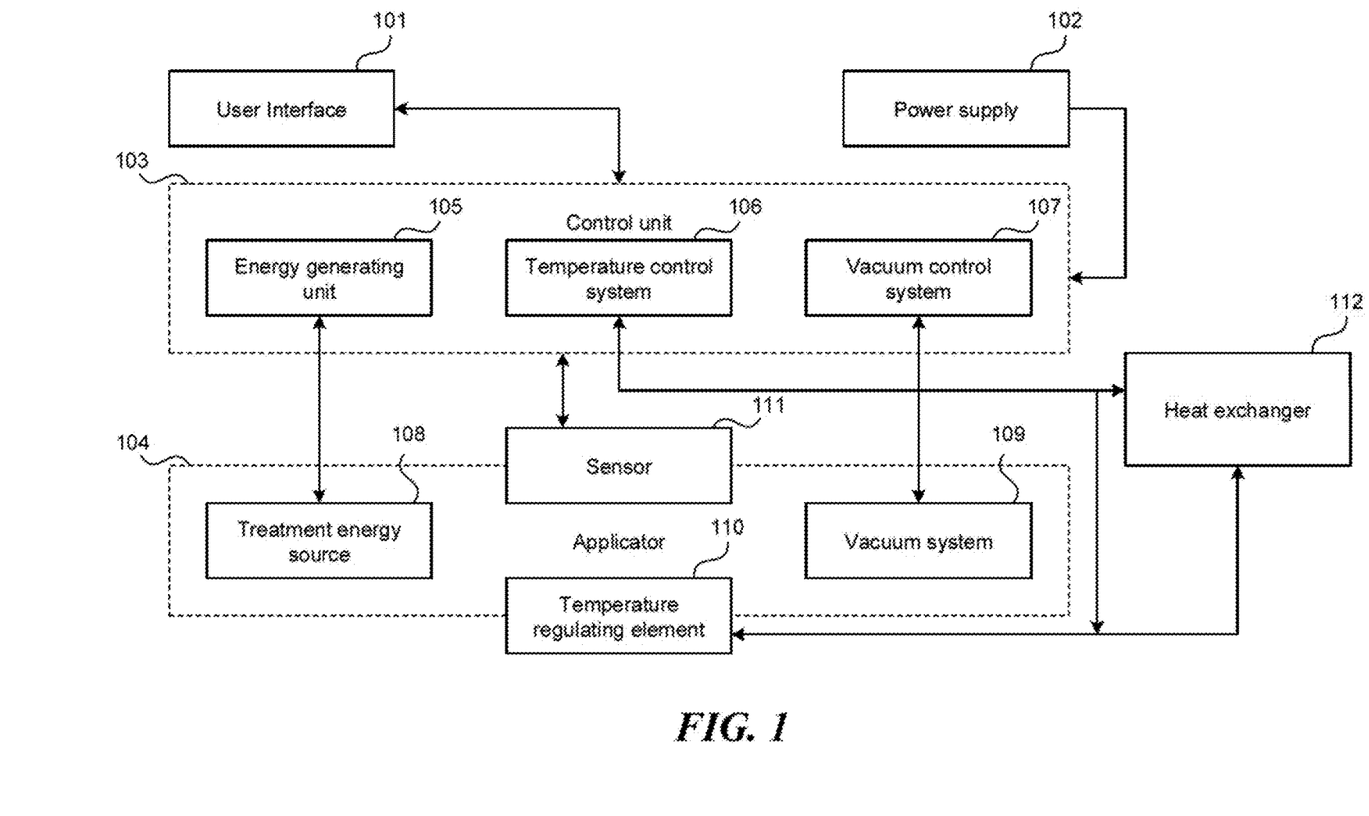
FIG. 1 is a schematic diagram of a treatment device.

As shown in FIG. 1, the device may include a user interface 101, a power supply 102, a control unit 103, an applicator 104 and other device hardware parts.

User interface 101 may be used for switching the device on/off, selection of a treatment protocol, setting treatment parameters (before and/or during the treatment) and/or as an information panel. User interface 101 may be connected to control unit 103 and/or control unit 103 may be part of the user interface 101. User interface 101 may be operated by touch display, other type of display, one or more buttons, joystick, by other control element and/or combination of thereof. Optionally user interface 101 may be also external device connected to a control unit wirelessly, by wire and/or optical fiber. Such external device may be e.g. a smartphone, computer and/or other device.

A power supply 102 may interact with control unit 103, energy generating unit 105, temperature control system 106, vacuum control system 107, other controlling mechanisms, treatment energy sources e.g. treatment energy source 108, vacuum system 109 and/or temperature regulating element 110; and/or other parts with need of power supply.

Control unit 103 may comprise an energy generating unit 105, a temperature regulating system 106 and a vacuum control system 107. The energy generating unit 105, the temperature regulating system 106 and the vacuum control system 107 may be part of the control unit 103 or may be as individual controlling mechanisms that may communicate with control unit 103, with each other and/or with other controlling mechanism and/or sensor. The energy generating unit 105, the temperature regulating system 106 and the vacuum control system 107 may consist of software part, hardware part and/or combination of software part with hardware parts. The controlling mechanism may be able to change specific parameters of delivered treatment energy to the patient body. The parameters may include frequency produced by the treatment energy source, pressure under the applicator, position of the applicator, output power of treatment energy source, pulse mode, temperature of the applicator's contact part with the patient, patient's temperature and/or others. Each of controlling mechanisms may change specific parameters according information sent by control unit 103, other controlling mechanisms, information sent from user interface 101, based on feedback information from at least one sensor and/or automatically according treatment protocol incorporated in controlling mechanism, control unit 103, or user interface 101.

The applicator 104 may include at least one treatment energy source 108, vacuum system 109, temperature regulating element 110, sensor 111 and/or other parts. A heat exchanger 112 may be localized in or outside of the applicator.

According another embodiment vacuum system 109, temperature regulating element 110 and/or sensor(s) 111 may be localized outside the applicator 104 (e.g. in the mother cases).

Control unit 103 may be located in the mother case as described in U.S. Provisional Application No. 62/375,796 incorporated herein by reference and/or in the applicator. Control unit 103 may comprise a separate or merged temperature control system 106 guiding temperature adjusting of the patient's epidermis, dermis, hypodermis, adipose tissue and/or temperature control system, energy generating unit, or vacuum control system.

Temperature control system 106 may provide guiding of at least one temperature regulating element 110 that regulates temperature of patient's soft tissue and/or any part of the device e.g.: the electrode, heat transmitter included in the heat exchanger 112, temperature of the material between treatment energy source and patient's body and/or any other part of the device.

Temperature regulating element 110 may include a passive temperature regulating element, active temperature regulating element or their combination.

A passive temperature regulating element may be an element changing temperature without need of input power supply e.g.: perforation of the applicator may provide cooling of any device by spontaneous air flow, material with high thermal conductivity removing heat by thermal diffusion between at least one part of the applicator and the environment spontaneously.

An active temperature regulating element may be an element changing temperature using an input power supply. An active temperature regulating system may be e.g.: heated or cooled fluid pumped to the applicator or in its proximity in order to adjust electrode temperature, a thermoelectric member adjusting temperature of any device part by the Peltier-Seebeck effect, heating coils heated by electric current, an element delivering sprayed coolant, ventilator and/or any other temperature regulating system.

Temperature control system 106 may cooperate with one or more sensors monitoring and/or contributing to evaluate temperature of the soft tissue and/or part of the device. Sensor or sensors contributing to evaluate temperature may not measure temperature as physical quantity but may measure a different physical quantity influenced by temperature and temperature may be calculated by using such influenced physical quantity. E.g. impedance of the soft tissue may change with changed temperature of such specific soft tissue part. Based on evolving impedance of the specific soft tissue part, temperature may be calculated by using a preprogrammed correlation function.

Temperature may be controlled with regard to the temperature of the e.g.: RF electrode; heat transmitter (may be any kind of fluid e.g.: water, $CO_2$, etc.); dielectric material as described below; the patient's epidermis, dermis, hypodermis, adipose tissue as visceral adipose tissue and/or subcutaneous adipose tissue.

Temperature control 106 system may adjust temperature of a heat transmitter in the heat exchanger 112 with gaseous or liquid heat transmitter.

The heat exchanger 112 and/or gaseous or liquid heat transmitter may optionally be omitted.

Heating/cooling of the patient's soft tissue (e.g.: epidermis, dermis, hypodermis and/or adipose tissue) may be provided by thermal diffusion between the applicator and the patient's body and/or by a treatment energy source providing heating of the patient's soft tissue by a different mechanism e.g.: RF waves, acoustic waves, plasma, muscle stimulation, friction, and/or other.

The device and method maintain optimal treatment temperature of the patient's surface (epidermis) in the range of 28-43° C. or 30-43° C. or 36-42° C.

In the present device and method the patient's epidermis may be heated to the temperature mentioned above in order to prevent heat shock of the patient's body. Any part of the applicator may be heated/cooled by itself and/or by temperature regulating element 110 and may regulate patient's surface temperature.

According to one embodiment patient's surface may be heated and/or cooled by thermal diffusion between a heated/cooled RF electrode and the patient's skin or surface, wherein a dielectric material, bolus filed with any fluid, textile layer active agent etc. may be located between the RF electrode and patient's surface.

If a temperature difference between patient surface and treated lower layers of the patient's soft tissue (e.g. hypodermis, visceral adipose tissue) is too high the treatment may be uncomfortable and/or painful. For example if patient's epidermis is cooled to 25° C. and patient's adipose tissue is heated to 48° C. then heat significantly and very fast diffuses from heated adipose tissue into the cooled area of the skin and treatment is inefficient, inhomogeneous and health risk may be increased.

Figure 2A:
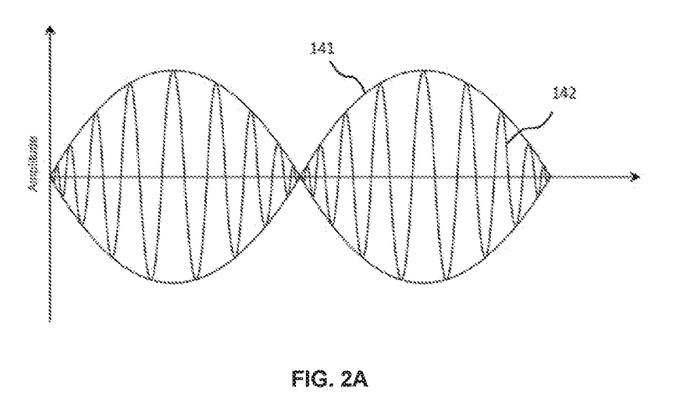
FIGS. 2A and 2B illustrate respectively an amplitude modulated wave having a sine envelope, and a frequency modulated wave.
Figure 2B:
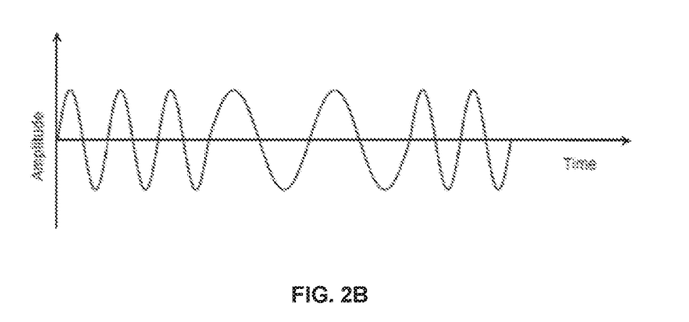

FIG. 2 are images from a thermos-camera that illustrate surface temperature after treatment provided by bipolar RF source. FIG. 2A demonstrates treatment by two applicators (according FIG. 6) where an electrode of each applicator was cooled below 25° C. FIG. 2B demonstrates treatment with the same applicators where electrode of each applicator was heated above 25° C. Cooled/heated electrodes according FIGS. 2A and 2B influenced temperature of the patient's epidermis and homogeneity of the treatment of hypodermis.

Heating the patient's surface to 25° C. or higher but lower than 43° C. (which is pain threshold) is very effective for improvement of homogeneity of the delivered RF treatment energy and energy distribution in the soft tissue. Heating the patient's surface also minimizes heat diffusion from the heated soft tissue (e.g. adipose tissue), which may improve effectiveness and homogeneity of the treatment and also may allow for shorter treatments Heating the patient's surface improves blood flow in the skin surface which improves dispersion of the heat in the skin surface, preventing creation of hot spots. Increased blood flow may locally accelerate body metabolism and also accelerate removing of damaged and/or dead cells. Such effect may accelerate results and reduce health risk. Increased blood flow may also improve selectivity of RF heating and filtering of unwanted/parasitic frequencies of the RF signal.

Heating of the patient's epidermis shows positive influence to the skin rejuvenation, increase skin elasticity and improvement of skin imperfections (e.g. structural inhomogeneity, stiffness of the scar). Heating of the patient's surface, namely dermis, with a combination of RF treatment, also improves results of cellulite removal and local acceleration of cell metabolism.

According to another embodiment cooling of the patient's epidermis below 20° C. may be provided. When skin surface temperature is decreased below 20° C. pain receptors may have lower sensitivity. With cooling of the patient's surface, it is also possible to increase output power of the treatment energy source 106 beyond the limit acceptable during treatment without regulation of the patient's surface temperature. This method requires optimal adjusting of delivered treatment energy parameters.

Optimal treatment temperature of the treated adipose tissue may be in the range of 41-48° C. or 41-47° C. or 42-45° C. The method and the device may be designed to provide many kinds of a treatment mostly based on apoptotic, necrotic destruction of adipose tissue and/or increasing adipose metabolism (catabolism). Therefore the treatment leads to reducing number and/or volume of adipose cells. Another therapy may be targeted to soft tissue layer (e.g. dermis) in order to start neocollagenesis and/or eleastogenesis (for e.g. wrinkle reduction, rejuvenation).

Heating of epidermis and/or other soft tissue structure (e.g. dermis, hypodermis, adipose tissue) may be provided continuously with continual heating or according to an arbitrary heating sequence until soft tissue temperature reaches a predefined tissue temperature. During continual heating treatment energy source output may be variable but temperature of the soft tissue rises until a predefined soft tissue temperature is reached. During the heating sequence the treatment energy source output may be variable. The temperature of the soft tissue may increase at least twice and also decrease at least once until a predefined temperature is reached.

Figure 3:
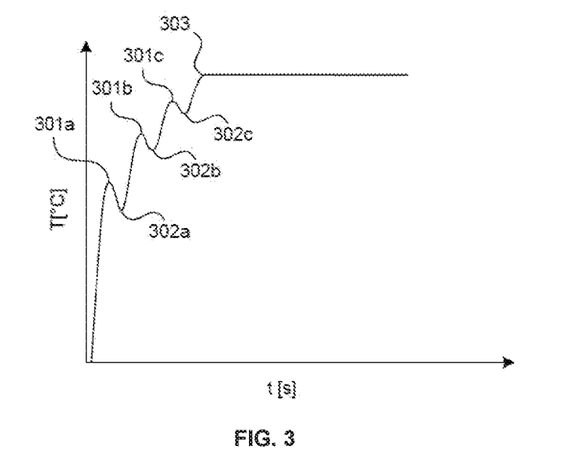
FIG. 3 is a graph of a heating sequence of the patient's surface.

FIG. 3 illustrates one possible temperature profile of the soft tissue. The vertical axis in FIG. 3 symbolizes temperature of the specific soft tissue layer (e.g. epidermis), and the horizontal axis symbolizes time. According to FIG. 3 at the beginning of the treatment a rapid rise of the temperature in the soft tissue may occur until the discomfort temperature level 301a is reached. Then temperature of the soft tissue (e.g. epidermis) may be reduced by at least 0.2° C. or a value between 0.2 to 4° C. or 05 to 3° C. or 1-2° C. to a comfortable temperature level 302a. Further temperate increases follow to a value of at least 0.2° C. or a value between 0.2 to 4° C. or 0.5 to 3° C. to a temperature higher than the prior maximal temperature of the discomfort level. Such heating profile may be practiced with multiple discomfort temperature levels e.g. 301b, 301c and multiple comfortable temperature levels e.g. 302b, 302c until a desired temperature 303 is reached. Between two discomfort temperature levels temperature of the soft tissue may not be reduced but may be kept constant for some time interval and then temperature of the soft tissue may be reduced or raised again. Temperature heating profiles may be guided by operator, by control unit 103 and/or by temperature control system 106, by energy generating unit 105 and/or by the treatment energy source.

Methods of heating described by FIG. 3 may be useful to adapt heat sensitive skin receptors to higher temperatures of the soft tissue than is normally comfortable, to prevent heat shock to patient's body, help to adapt patient's body to treatment, stabilize biological processes during the treatment and/or may enable reaching therapeutic desired temperature 303 in the soft tissue in shorter time.

According to another embodiment a heating profile of the patient's soft tissue reaching predefined optimal treatment temperature may be at least partially exponential. After reaching of the certain predefined temperature and/or after specific time delay heating and/or cooling may be slowed and temperature of the soft tissue may be kept constant. Priority of such heating profile is to reach optimal treatment temperature as soon as possible and/or on the higher temperature value than is comfortable without such heating profile.

According to another embodiment a heating profile of the patient's soft tissue in time may be at least partially by logarithmic, linear, periodical, or polynomial functions and/or a combination of these functions where variables are temperature and time.

Time needed to reach optimal soft tissue treatment temperature according to the proposed device and method is after 7 minutes, more preferably after 4 minutes, more preferably after 2 minutes, more preferably after 1 minute, even more preferably after 50 s, even more preferably after 40 s, even more preferably after 30, most preferably after 5 s after treatment start. The therapeutic desired temperature may be kept for 0.05-30 minutes or 0.2-25 minutes or 0.5-20 minutes or 0.2-18 minute.

The device and method produce temperature difference $\Delta T_1$ between a contact part of the applicator and treated adipose tissue. Temperature difference $\Delta T_2$ is created between epidermis and treated adipose tissue. Temperature difference $\Delta T_3$ is created between epidermis and non-adipose tissue in dermis. Absolute values of the temperature difference $\Delta T_1$ may be in the range of 0-18° C. or 0-15° C. or 3-15° C. or 2-10° C., wherein the adipose tissue has a temperature preferably higher than a contact part of the applicator. Absolute values of temperature difference $\Delta T_2$ may be in range of 0-18° C. or 0-10° C. or 2-7° C., wherein the adipose tissue has preferably a higher temperature than the epidermis. Absolute values of temperature difference $\Delta T_3$ may be in the range of 0-18° C. or 0-10° C. or 2-8° C.

The heating source of the applicator may be a thermally regulated RF electrode and/or a dielectric material located between treatment energy source and patient's surface (epidermis). The thermal gradient between the RF electrode surface and the patient's surface may be in range between 0-15° C. or 5-12° C. or 8-12° C. A thermal gradient between the RF electrode surface and the patient's surface may be influenced by a dielectric material that may be localized between the RF electrode and the patient's surface. Thermal conductivity of the dielectric material at 293° Kelvin may be in range 0.05 to 1 $W \cdot m^{-1} \cdot K^{-1}$ or in range 0.1 to 0.5 or in range 0.1 to 0.3.

The device may comprise one or more sensors providing feedback information to control unit 103, user interface 101 and/or to an individual controlling mechanism. Based on evaluated feedback information, treatment parameters may be adjusted by control unit 103, by a user and/or by any controlling mechanism. A sensor may be located in a heat exchanger, system enclosure and/or in the applicator. Sensors n the device may measure: pressure under the applicator, temperature, viscosity of heat transmitter, flow of the heat transmitter, impedance, capacity, permittivity, conductivity, susceptibility of any part of the device and/or patient's body, sensors analyzing backscattered signal, infrared radiated spectrum and its intensity, heat capacity, voltage, electric current, phase shift of delivered and backscattered signal of treatment energy, pulse of the patient and any other biological, biochemical and/or physical parameter e.g.: skin tension, muscle tension, level of muscle contraction, amount of perspiration, breathing frequency, etc.

Temperature of the soft tissue may be measured by a sensor directly evaluating temperature as a physical quantity (e.g. thermometer, thermal imager, etc.) Another method to evaluate temperature may be by measuring a different physical quantity other than temperature, wherein the physical quantity is thermally dependent (e.g. by measuring impedance of the soft tissue beneath the epidermis and counting soft tissue temperature based on a correlation function that describes such soft tissue dependence of impedance on temperature). Indirect methods of measuring soft tissue temperature may be beneficial to evaluate noninvasively temperature of the soft tissue under the epidermis, dermis and/or hypodermis.

According to another embodiment cooling of the patient's epidermis below 20° C. may be provided. When skin surface temperature is decreased below 20° C. pain receptors may have lower sensitivity. With cooling of the patient's surface it is also possible to increase output power of the treatment energy source 106 beyond the limit that is acceptable during treatment without regulation of the patient's surface temperature. This method requires optimal adjusting of delivered treatment energy parameters in order to provide optimal homogeneity treatment.

Figure 4:
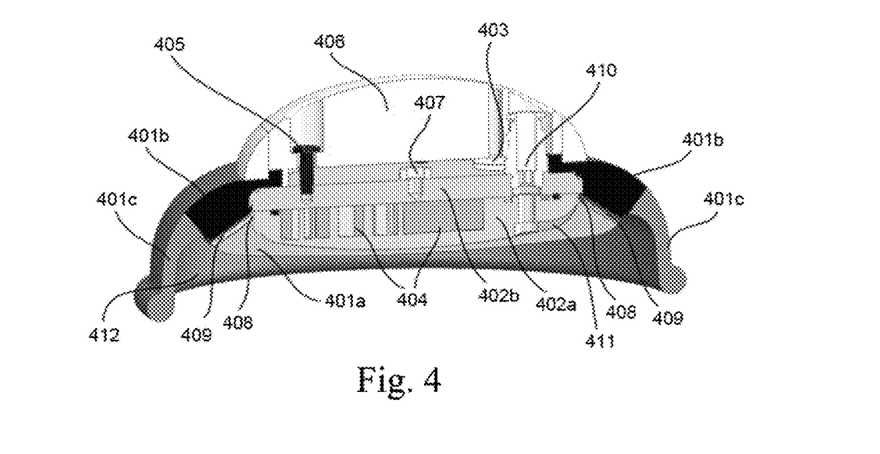
FIG. 4 is a perspective section view of an applicator.

As shown in FIG. 4, an applicator may have one RF electrode with upper part 402b and lower part 402a. The RF electrode may include one or more cavities 404 with the same or different volumes. Cavity 404 may be filled by heat transmitter through the inlet/outlet aperture 403 in order to regulate electrode temperature or physical properties.

RF electrode 402a-402b may be at least partially covered by dielectric material which may be divided into parts 401a, 401b and 401c. Part 401a is dielectric material located under and on the side of the RF electrode (especially lower part 402a of the RF electrode). Part 401b may fix the dielectric material to other parts of the applicator and also may hold other applicator parts together. Part 401c is a vacuum edge that in combination with supplied vacuum under the applicator may attach the applicator to the patient's surface. Dielectric material with parts 401a-401c may be designed as individual parts 401a, 401b and 401c or as one piece.

Vacuum may be delivered under the applicator by at least one inlet/outlet vacuum aperture 410. This aperture may go through the electrode around the electrode and/or through the part 401a, 401b or 401c of the dielectric material directly into the cavity 412 under the applicator. According to FIG. 4 vacuum aperture 410 go through the RF electrode to the vacuum guide 411 leading to vacuum channel 408 in the electrode and/or in the dielectric material. Vacuum channel 408 redistributes vacuum around the electrode and to the vacuum pipe 409. Dielectric material may include one or more vacuum pipes 409 applying vacuum to the cavity 412 under the applicator.

Isolating elements as an upper applicator lid 406 and an isolation for power supply cable 407 may be attached to the electrode.

Individual parts of the applicator may be connected by connecting member 405 (e.g. screws, glue, snapped to each other, molded to each other, connected by vacuum and friction forces, fixed by interaction between polar and non-polar groups of different materials and/or may be hold to each other by magnetic and/or electromagnetic forces as described in U.S. Provisional Application No. 62/375,796 incorporated herein by reference.

According to one embodiment at least two parts of the applicator may be connected together by dielectric material, e.g. in FIG. 4 dielectric material including parts 401a-401c may hold together lid of the applicator 406 upper and lower part of the RF electrode 402b and 402a without need of screws and/or other fastening mechanism.

The method and device may be based on capacitive RF heating of the soft tissue by bipolar and/or multipolar electrode arrangement with applied vacuum under the applicator and controlled heating of the patient's surface by thermal diffusion. One applicator may include one or more electrodes. The device may also include none, one or more RF electrodes heating the soft tissue by RF inductive heating e.g. heating of collagen fibers. The device may include at least one applicator. According another embodiment RF electrode(s) may be substitute and/or replenish by other source of energy than RF source of energy (e.g. by ultrasound transducer, light energy source and/or other).

The RF electrode(s) may exhibit multipolar system behavior where at least one electrode is connected with RF energy flux density between at least two another electrodes. One RF electrode and/or group of RF electrodes including at least two RF electrodes may be switched on/off according treatment pattern as it is described in U.S. Provisional Application No. 62/375,796 incorporated herein by reference.

The distance between edges of the RF electrodes' treatment energy sources may be at least 1 cm and/or be in the range from 1 cm to 40 cm, or 1 cm to 25 cm or 5 cm to 20 cm.

Target depth of the RF treatment energy may be between 0.1 cm 20 cm or between 1 cm to 20 cm or between 1.5 cm to 12 cm or between 2 cm and 8 cm in the patient's soft tissue.

According to a preferred embodiment the device includes even number of the applicators wherein each applicator includes one electrode (see FIG. 4). Two of such applicators exhibit bipolar system behavior with adjustable RF energy flux density between electrodes of the applicators.

One or more electrodes may have different sizes and shapes that influence size of treated area, focus of the treatment, parameters of provided treatment energy and/or homogeneity of the treatment. Electrodes may be formed by conductive wire or system of wires, by a conductive plate and/or other conductive or semi-conductive object. Shapes of electrodes may be asymmetrical or at least partially symmetrical e.g.: oval, elliptical, planar, square, wavy, convex, concave, spiral and/or other shape of electrode and/or shape of electrode surface. The electrode may consist of one or more pieces. The electrode with rounded edge(s) may minimize edge effect and prevent hot spots creation. According to a preferred embodiment an RF electrode has a circular contour in longitudinal cross section and at least partly elliptical shape of lower part of the electrode 402a in vertical cross section, as shown in FIG. 4.

Diameter of the RF electrode in FIG. 4 may be in the range from 0.6 cm to 40 cm or from 6 cm to 30 cm or from 6 cm to 15 cm or may have any other diameter.

The RF electrode of the device may have different sizes and shapes. Surface size of the RF electrode contacting the patient (see lower part of the electrode 402a FIG. 4) may be in range between 1 $cm^2$ to 1200 $cm^2$ or between 10 $cm^2$ to 800 $cm^2$ or between 30 $cm^2$ to 300 $cm^2$ or 30 $cm^2$ to 100 $cm^2$.

Figure 5:
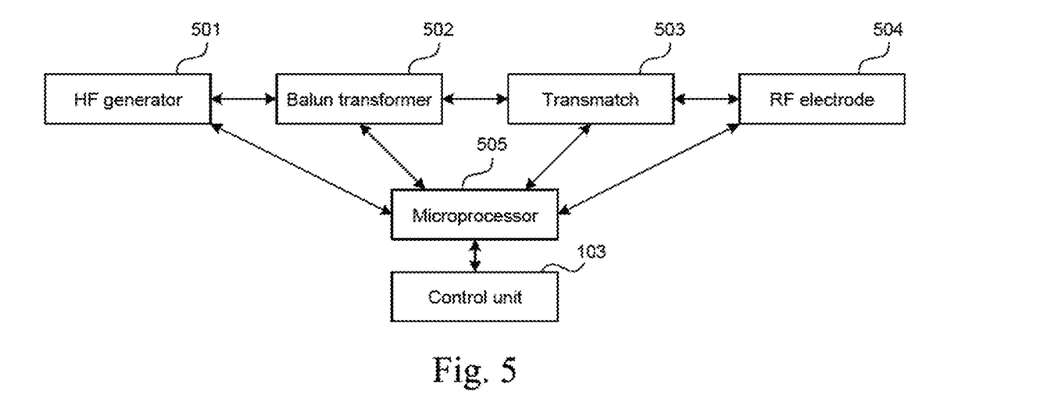
FIG. 5 is a schematic diagram of an RF-regulating system

In order to provide improve adjustment of delivered treatment energy parameters may be used RF-regulating system (see FIG. 5). RF-regulating system may be part of treatment energy source 108 and/or energy generating unit 105. RF-regulating system may include any part from the FIG. 4. e.g.: may include a HF generator 501, balun transformer 502 that converts between balanced or unbalanced signal, impedance matching circuit (e.g. transmatch) 503, RF electrode 504 and/or microprocessor 505. RF-regulating system may communicate with control unit 103 or may be part of it.

According another embodiment microprocessor 505 and/or other part of RF-regulating system may not be included or may be part of other controlling mechanism.

HF generator may be regulated in order to increase amplitude of delivered treatment energy signal and so increased output power of the treatment energy source.

Balun transformer may transform balanced signal to unbalanced and vice versa. Balun transformer may transform signal before and/or after adjusting signal by transmatch.

Transmatch may adjust frequency of treatment energy signal to optimize selective heating of targeted tissue with minimal signal back scattering and heating of unwanted soft tissue structure.

RF electrodes providing capacitive heating of the soft tissue creates with treated soft tissue imaginary capacitor. In order to improve adjustment of delivered treatment energy parameters and capacity of such imaginary capacitor may be adjusted active surface of the electrode. RF electrode as treatment energy source may include apertures. Size of the electrode's apertures may be varied and so capacitance of imaginary condenser. Adjusting of RF electrode surface may be also provided by other mechanism described in U.S. Provisional Application No. 62/351,156, incorporated herein by reference.

In order to prevent edge effect, improve focusing and homogeneity of provided RF energy into the soft tissue dielectric material part 401a may be profiled. Profiled part 401a of dielectric material may be thinner below the center of the RF electrode than below the RF electrode edge. Thickness of profiled part 401a of dielectric material below the center of electrode may be in range from 0.1 mm to 10 cm or from 0.5 mm to 1 cm or from 1 mm to 5 mm. Dielectric material below the electrode's edge may be thick in range from 0.2 mm to 12 cm or from 1 mm to 3 cm or from 2 mm to 1 cm. Thickness of the dielectric material part 601a below the electrode's edge may be or at least 5% or 10% or 20% or 50% or 100% or 300% thicker than is dielectric material below the center of RF electrode.

According another embodiment profiled part 401a of dielectric material may be substitute by non-profiled part 401a of dielectric material with different dielectric properties at the edges than dielectric properties at the center below the RF electrode.

According another embodiment some part of dielectric material, namely part 401a, may include one or more cavities inside. Cavity inside dielectric material may be filled with a heat transmitter (e.g., water or similar substance) and may be thermally regulated and/or may change dielectric properties of such dielectric material part.

Part 401c of dielectric material called vacuum edge or vacuum cup may define magnitude of patient's skin protrusion, pressure value needed for attaching applicator to patient's body and other properties. Vacuum edge 401c may have a circular, rectangular or other symmetrical or asymmetrical shape.

Dielectric material parts 401a-401c may be rigid, at least partly shape adaptive and/or at least partly elastic. Dielectric material from at least partly shape adaptive material may provide flexibility to adapt applicator surface to patient's surface and improve contact of the dielectric material with electrode and/or the patient body. Shape adaptive material(s) may also improve energy transfer from applicator to patient's soft tissue. Dielectric material under the RF electrode may be any kind of polymeric material and/or blend of multiple materials with specific dielectric parameters (e.g.: silicone, latex, rubber and/or other).

According FIG. 4 dielectric material may include parts as 401a, 401b and 401c. Dielectric material in the applicator may be created as one piece including parts as vacuum edge 401c, dielectric layer under the treatment energy source 401a (e.g. RF electrode) and/or at least part of the applicator covering 401b. According another embodiment dielectric material may be composed of individually fabricated several parts e.g. parts 401a, 401b and 401c. Individual parts or segments of dielectric material (e.g.: 401a, 401b, 401c) may have the same or different mechanical, chemical, electrical, and/or magnetic properties (e.g. elasticity, stiffness, durability, dielectric constant, biocompatibility, etc.).

Optionally applicator may include flexible shape changing and/or elastic polymeric dielectric material as one piece including parts 401a, 401b and 401c which may provide better adaptiveness of the applicator to patient's body, better integrity of applicator and easy way how to exchange this part which may be in contact with patient during the treatment. Exchangeability of dielectric material may be convenient to improve hygiene of the treatment, personalization for individual patients and application needs and decrease costs of exchange worn applicator parts. According to one embodiment dielectric material may be exchange for another one and/or removed without need of screws and/or technical knowledges.

Stiffness of the dielectric material may be in range shore A5 to shore D80 or shore A5 to shore A80 or shore A10 to shore A50 or shore A10 to shore A30. Dielectric material may be made of different polymeric characterization.

Dielectric constant of the dielectric material namely part 401a without fluid inside may be in range from 1.5 to 12.5 or from 2 to 10 or from 2 to 7 or from 2 to 4 under the electromagnetic field with frequency 50 Hz.

Dielectric material (spacing object) located between patient's soft tissue surface and treatment energy source may have specific properties and influence parameters of treatment energy as it is described in U.S. Provisional Application No. 62/331,072 is incorporated herein by reference.

According another embodiment some part(s) of dielectric material may be omitted, e.g. dielectric material under the treatment energy source.

Vacuum (lower air pressure than is air pressure in the room) may be used for attaching of the applicator to a certain patient's body part, may regulate contact area size of dielectric material under the treatment energy source with the patient's surface, may provide massage of the patient's soft tissue, may help to reduce creation of hot spots and edge effect, may increase body liquids circulation and/or different protrusion shapes.

Regulation of vacuum may be provided in mother case in the applicator and/or on the way between mother case and applicator. Regulation of the vacuum brought under the applicator may be executed by valve, by construction of the device (mainly applicator) and/or by system regulation of output power of vacuum system.

Figure 6:
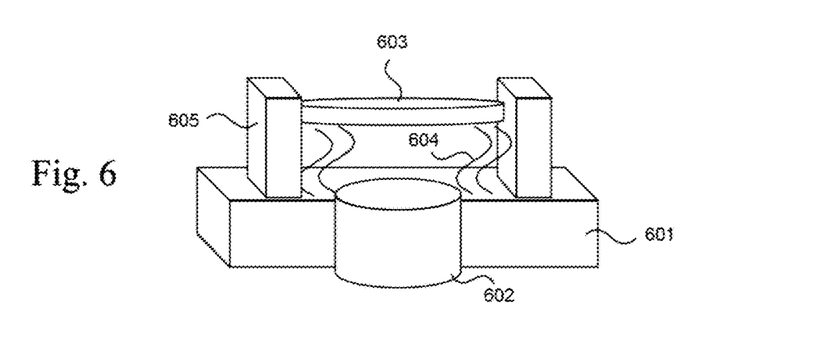
FIG. 6 illustrates a valve embodiment.

The device may include one or more valves. Valves may be controlled by control unit and/or may be self-controlled depending on the air pressure value in the cavity under the applicator and on the other side of the valve closer to vacuum pump. One possible embodiment of self-controlled valve is illustrated in FIG. 6. FIG. 6 illustrates vacuum inlet/outlet aperture 602 located in wall 601 dividing environments with different pressure value. The aperture is closed by closing object 603 pushed by springs 604 against the wall 601 or by other mechanism. Springs 604 may be fixed in closing object 603 and wall 601 or to other part of the valve. Closing object 603 may be moved along rails 605 defining the movement path of the closing object 603. If air pressure on the valve side closer to the cavity under the applicator exerts higher force to closing object 603 than springs from the other side of the closing object 603 then valve is closed, if not the valve is opened. Opening and closing valve may be based on different principle e.g. as one described above, regulating applied vacuum may be based on increasing/decreasing diameter of aperture 602 and/or by another principle.

According another embodiment the device does not need to use any type of valve in the applicator. Design, material and number of device parts that are involved to delivering of vacuum under the applicator may regulate air pressure under the applicator also without any valve. According one of possible applicator embodiment illustrate by FIG. 4, the vacuum value (lowest air pressure) distributed to the cavity 412 under the applicator with constant output power of vacuum system may be influenced by number and/or diameter of vacuum pipe 409, inlet/outlet aperture 410, vacuum guide 411 and/or by channel 408.

According to another embodiment the applicator may be designed so that vacuum under the applicator may change cross-section area of vacuum guiding part and influence air pressure value under the applicator. Change of vacuum guiding part cross-section area and/or shape may be caused by expansion, shape change and/or deformation of material(s) which the part is made of.

Figure 7A:
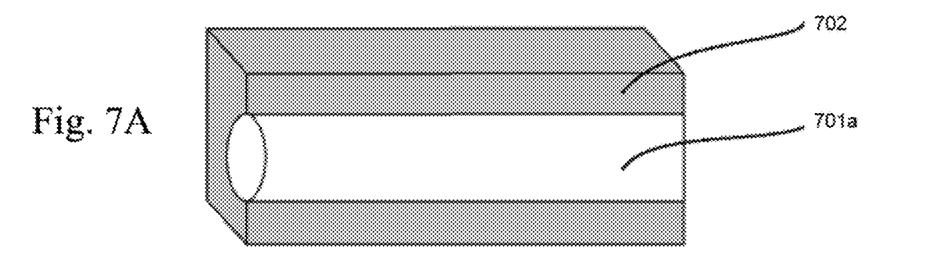
FIGS. 7A and 7B are diagrams illustrating shape change of a vacuum guiding part that may regulate vacuum level.
Figure 7B:
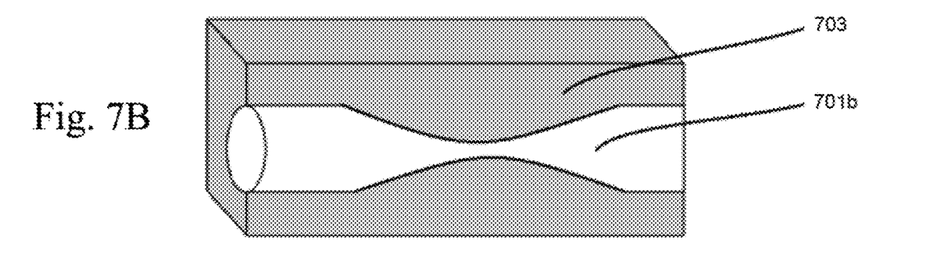

One example of expansion, shape change and/or deformation of vacuum guiding part may be FIG. 7 where 701a is an aperture of guiding vacuum part 702 during normal air pressure in the aperture 701a and 701b is an aperture of guiding vacuum part 703 during decreased air pressure in the aperture 701b.

Figure 8A:
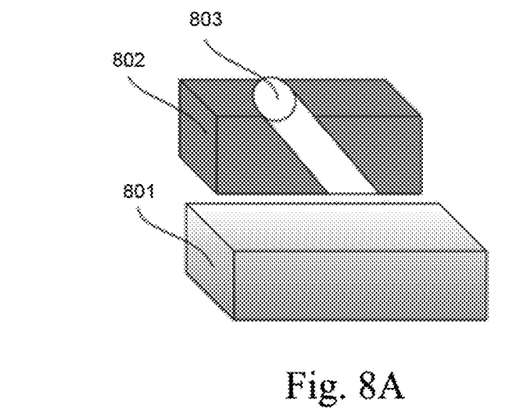
FIGS. 8A and 8B illustrate deformation of a vacuum guiding part that may regulate vacuum level under the applicator.
Figure 8B:
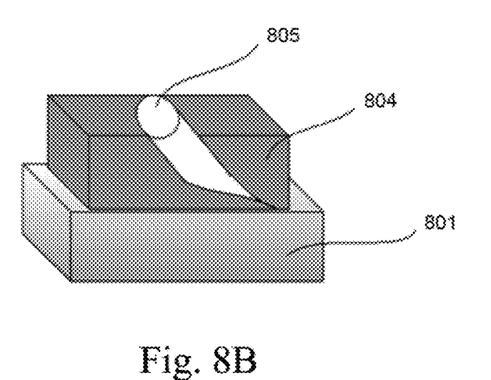

Another example of expansion, shape change and/or deformation of device part involved to delivering of vacuum under the applicator may be FIG. 8 where 801 is the patient's skin or surface, 802 dielectric material including vacuum pipe 803 with no contact with patient's surface and 804 is a dielectric material in contact with patient's surface that deformed vacuum pipe 805 by pressure of the patient's surface.

Vacuum under applicator may be constant and/or may be changed during the treatment time.

Constant air pressure under the applicator may be provided by continual pumping air out of the applicator. According one embodiment providing constant air pressure lower than atmospheric pressure, vacuum system is operating during whole treatment and is not regulated by any valve. At the beginning of the treatment applicator attached to patient body and may be fixed to specific area. After fixing applicator to patient's surface vacuum system output power is decreased to a value where air amount pervade from the outside of the applicator to cavity 412 below the applicator is in balance with amount of sucked air from the cavity 412 below the applicator.

In other embodiment and/or treatment protocol vacuum output power may be constant during at least part of the treatment, creating equilibrium between air pervading into the cavity below the applicator and air sucked out of the cavity, provided by the diameter and length of the vacuum related device parts under the applicator (e.g. 409 and/or 410 see FIG. 4). The mechanism of such equilibrium is based on air friction and turbulence in the narrow device parts.

Another mechanism for keeping constant pressure under the applicator is to regulate opening, closing and/or changing inlet/outlet aperture of the valve(s) when the pressure under the applicator is changed.

Constant pressure under the applicator may be provided by increasing output power, decreasing output power and/or switching on/off of the vacuum system.

Pressure under the applicator may be changed during the time of the therapy. Changing pressure value under the applicator may be cyclically repeated during the therapy. Such effect may be used as massage of the adjacent soft tissue. Massage of the adjacent soft tissue in combination with RF treatment energy source may accelerate treatment effect, improve treatment results and decrease health risk. Massage of soft tissue improve lymph and blood flow that improve heat distribution in the adjacent soft tissue that lower risk of creating hot spots and thermal inhomogeneity on the patient's surface. Massage in combination with RF treatment energy source may accelerate fat metabolism, elastogenesis and/or neocalagenesis. Massage may stimulate movement of body fluids, as described in U.S. patent application Ser. No. 15/433,210, incorporated herein by reference.

Cycle changing pressure value under the applicator may be provided by increasing/decreasing output power of vacuum system, by changing diameter of inlet/outlet aperture for pumped air out of the cavity below the applicator, by closing/opening of at least one valve and/or combination thereof.

Changing pressure value under the applicator may change contact area of the dielectric material 401a or RF electrode with patient's surface. According one embodiment changed pressure value under the applicator changes protrusion of the soft tissue between vacuum edge 401c and dielectric material part 401a. This may also change targeting and/or amount of delivered treatment energy source on the edge of the treatment energy source (e.g. electrode) that may also prevent edge effect, creating of hot spots and other health risks.

Pressure value under the applicator may be changed compare to pressure in the room during the treatment in range from 0.1 to 100 kPa or from 0.2 kPa to 70 kPa or from 0.5 kPa to 20 kPa or from 1 kPa to 10 kPa or from 2 kPa to 8 kPa.

The applied negative pressure may be continual or pulsed. Continual pressure means that the pressure amplitude is continually maintained after reaching the desired negative pressure. The pulsed pressure means pressure where the pressure amplitude varies during the therapy. The pulsed negative pressure may alternate with peak pressure differences from 0.1 kPa to 100 kPa with regards to pressure in the room (atmospheric pressure), more preferably form 2 kPa to 20 kPa with regards to pressure in the room (atmospheric pressure), most preferably from 2 kPa to 10 kPa with regards to pressure in the room (atmospheric pressure). The duration of one pulse is in range between 0.1 s to 1200 s or 0.1 s to 100 s or 0.1 s to 60 s or 0.1 s to 10 s; wherein the pulse means duration between two beginnings of successive increases or decreases of negative pressure value.

In case of using pulsed pressure the ratio of $P_h/P_l$ where $P_h$ is value of highest pressure value a $P_l$ is lowest pressure value during one cycle of repeated pressure alteration may be in range from 1.1 to 30 or from 1.1 to 10 or from 1.1. to 5.

Placing, holding of the applicators adjacent to the patient's body and switching between them may be provided as described in U.S. Provisional Application No. 62/358,417 incorporated herein by reference and/or in in U.S. Provisional Application No. 62/375,796 incorporated herein by reference.

The present device and method may provide different types of energies in order to provide treatment as described above. The device preferably uses an RF treatment energy source.

Waves of the RF therapy may be delivered in the range from 0.5 MHz to 100 MHz.

According another embodiment RF waves in microwave range from 300 MHz to 300 GHz may have several benefits namely in combination with dielectric material 601a located between treatment energy source and patient's soft tissue surface. Advantages and parameters of treatment may be used as described in U.S. Provisional Application No. 62/331,072 incorporated herein by reference.

An electromagnetic field may be applied to the patient body in continual and/or pulse modes. Continual irradiation of a body area by RF may be at least 5 s or 20 s or 30 s or 60 s or 120 s or 240 s or 10 minutes or 20 minutes or more than 20 minutes or the most preferably more than 35 minutes.

The pulsed electromagnetic field may last between 50 μs to 100 s, in more preferred protocol pulse may last between 1 s to 70 s, and in the most preferred embodiment pulse may last between 3 s to 70 s.

An RF treatment energy source may be adjacent to the patient's soft tissue in contact mode where RF treatment energy source (electrode) is in contact with the patient's surface, indirect and/or in no-contact mode, i.e., with the electrode not in contact with the patient surface.

Energy flux density (energy flux density on the electrode surface) of the electromagnetic field in noncontact mode, where electrodes providing RF signal are spaced from the patient body by an air gap may be preferably in the range between 0.01 mW·mm−2 and 10 W·mm−2, more preferably in the range between 0.01 mW·mm−2 and 1 W·mm−2, most preferably in the range between 0.01 mW·mm−2 and 400 mW·mm−2.

Energy flux density of the electromagnetic field in contact mode (including the direct contact of electrodes coated by thin layer of insulator) may be preferably in the range between 0.01 mW·mm−2 and 2000 mW·mm−2, more preferably in the range between 0.01 mW·mm−2 and 500 mW·mm−2, most preferably in the range between 0.05 mW·mm−2 and 280 mW·mm−2.

Energy flux density of the electromagnetic field in non-contact mode where electrode is spaced from the patient body by dielectric material with beneficial dielectric parameters e.g.: using a spacing member such a flexible container holding a bolus of water, silicon and/or others dielectric materials) may be preferably in the range between 0.01 mW·mm−2 and 500 mW·mm−2, more preferably in the range between 0.01 mW·mm−2 and 240 mW·mm−2 or even more preferably in the range between 0.01 mW·mm−2 and 60 mW·mm−2 or the most preferably in the range between 0.05 mW·mm−2 and 12 mW·mm−2.

RF electrode may operate in capacitive and/or inductive mode.

According to preferred embodiment capacitive mode providing selective and safe treatment may include RF-regulating system (see FIG. 11). RF-regulating system may be part of the energy generating unit 105, control unit 103 and/or may be located individually and may communicate with control unit 103.

Parameters of RF treatment energy may be also modulated (adjusted) as described in U.S. Provisional Application No. 62/333,666 incorporated herein by reference. An example of amplitude modulation of a continuous wave 142 with a sine envelope 141 is shown in FIG. 2A. An example of frequency modulation of a continuous wave is shown in FIG. 2B. An alternative embodiment applicator may be movable as described in U.S. Provisional Application No. 62/331,088 incorporated herein by reference.

According to still another embodiment muscle stimulation or other soft tissue structures stimulation by electrical current and/or by magnetic field may be also used as type of soft tissue massage. Muscle stimulation may improve targeting of heating up of soft tissue, provide better homogeneity in delivered energy, prevent local hot spots, improve blood and lymph circulation and/or influence dielectric properties of specific soft tissue layers (e.g. may synergistically influence transfer of RF waves into the soft tissue). Repeated muscle contraction accelerates body metabolism, heats up adjoining soft tissues, stimulates secretion of several hormones, may change polarity of some soft tissue structures that influence transfer of RF energy into the soft tissue and/or may be beneficial for body shaping as reducing adipose cell volume, muscle building, muscle strengthening. Muscle contraction causes massage of adjoining soft tissue structure and cause massage of the deep soft tissue layers without affecting the surface of the patient.

Different nerves and soft tissue structures may be stimulated using interferential electrotherapy with a medium frequency in the range of 500 Hz to 12 kHz or in a more preferred embodiment in the range 500 to 8 kHz, in the most preferred embodiment in the range 500 to 6 kHz, creating pulse envelopes with frequencies for stimulation of the nerves and tissues e.g. sympathetic nerves (0.1-5 Hz), parasympathetic nerves (10-150 Hz), motor nerves (10-50 Hz), smooth muscle (0-10 Hz), sensor nerves (90-100 Hz), nociceptive fibers (90-150 Hz).

Muscle stimulation may be provided by e.g. intermittent direct currents, alternating currents (medium-frequency and TENS currents), faradic current as a method for multiple stimulation and/or others. Frequency of the currents and/or its envelope is typically in the range from 0.1 Hz to 200 Hz in preferred embodiment or from 0.1 Hz to 150 Hz in more preferred embodiment or from 0.1 to 140 Hz in the most preferred embodiment.

The method of nerve/muscle stimulation by magnetic field may use a peak to peak magnetic flux density on a coil surface at least 0.2 T, 0.4 T, 1.5 T, 2 T, at least 3 T, or up to 7 T. The repetition rate may be 1 Hz-700 Hz or more preferably 1 Hz-300 Hz or most preferably 1 Hz-200 Hz, with initial or successive treatments lasting several seconds or longer, for example, for at least 5, 10, 30, 60, 120 or 240 seconds, or longer. The pulse width is in the range of tens to hundreds of microseconds.

Stimulation of patient's soft tissue by magnetic field and/or electric field may be used with or without contact of such treatment energy source with the patient's surface.

A treatment energy source may also provide another treatment by a generated magnetic field and/or electric current. The most preferred frequency ranges for individual types of treatment are:

1) 2-10 Hz—endogenous opioid theory—chronic pain management;
2) 60-100 Hz—gate control theory—acute pain management;
3) 120-140 Hz—peripheral pattern theory—subacute pain management;
4) 5 and 150 Hz—fracture healing;
5) 45 Hz—joint mobilization;
6) 2-70 Hz—myostimulation.

RF treatment energy source combined with at least partial muscle stimulation may have also other convenient parameters and effects as it is described in U.S. Provisional Application No. 62/340,398 incorporated herein by reference.

According another embodiment the device may provide treatment by plasma and/or by combination of plasma with another treatment energy source e.g. RF treatment energy source. Plasma may be also supplemented with substances enhancing generation of plasma and/or treatment results as described in U.S. Provisional Application No. 62/409,665 incorporated herein by reference.

According another embodiment treatment may be further influenced and improved by an active agent substance (e.g.: gas, gel, liquid, suspension) that may make treatment more comfortable (e.g. less painful), faster, treatment may have better results and/or may make treatment more targeted. Active agent may be supplied before during and/or after treatment automatically by the device itself and/or by a person supervising the treatment.

In addition, the supplied mixture (e.g. green tea extract) may include other substances. Application of the substance and/or mixture of the substances may provide patient with a more comfort and/or improve the treatment effect.

In one embodiment, the substance may modulate normal metabolism and/or basal metabolism rate of the patient's body. It may provide acceleration to the metabolism related to the apoptotic cells. Such substances may include alkaloids (e.g. xanthines), antithyroid agents, metformin, octreotide and a like.

In another embodiment, the substance may modulate efferocytosis, which is the process by which dying cells are removed by phagocytic cells. This may provide acceleration and improvement in the dead cells removal. Such substance may include prostaglandins and their analogues, modified lipids (e.g. lysophosphatidylserine, lipoxins, resolvins, protectins and/or maresins), lipoprotein lipase inhibitors, nitric oxide secretion stimulators, alkaloids (e.g. xanthines), aspirin, antioxidants (e.g. ascorbic acid), derivatives of carbohydrates and a like.

In another embodiment, the substance may modulate lipolysis rate. In case of application of electromagnetic energy to the adipocytes it may provide another way of removal of the adipose cells, which may be independent from the treatment method. Such substances may include terpens (e.g. forskolin), catecholamins, hormones (e.g. leptin, growth hormone and/or testosterone), alkaloids (e.g. synephrin), phosphodiesterase inhibitors (e.g. xanthins), polyphenols, peptides (e.g. natriuretic peptides), amino acids and a like.

In another embodiment, the substance may modulate hydration of the patient. Such substances and/or mixtures may include xanthines, lactated Ringer's solution, physiological saline solution and a like.

In another embodiment, the substance may modulate circulatory system of the patient. This may provide the higher rate of blood circulation, which may result in faster cooling rate of the skin. Such substances may include catecholamines, alkaloids (e.g. xanthins), flavanols and a like.

In another embodiment, the substance may induce the reversible decrease or absence of sensation in the specific part of the patient's body. This may provide a certain level of comfort to heat-sensitive patient. Such substances may include lidocaine, benzocaine, menthol and a like.

In another embodiment, the substance may shield the electromagnetic radiation from the patient's body. This effect may be used for protection of sensitive parts of the human body. Such substances may include mixture containing metal nanoparticles, mixture containing polymer particles and a like.

In another embodiment, the substance may modulate the effect the electromagnetic radiation applied on the patient's body. This may accelerate removal of the desired tissue, for example by heating of the tissue and/or increasing the effect of the applied radiations. Such substances may include carotens, chlorophylls, flavanols and a like.

Substances may be used singularly or in various combinations with at least one other suitable substance. For example, lidocain providing local anesthesia may be combined with prilocaine to provide improved effect. The substance and/or mixture of the substances may be administered at different times during the tissue treatment. It may be administered before the treatment, during the treatment and after the treatment.

In another embodiment, the substance may be administered over seconds, hours or even days to accumulate in the desired tissue. The subsequent application of the electromagnetic radiation may modulate the action of the accumulated substance and/or be modulated by the action of the substance. According the example of this embodiment, a chromophore may be accumulated in the treated tissue, such as adipocytes, before the treatment. The chromophore may then absorb electromagnetic radiation and heat the tissue nearby.

Such active agents may influence the treatment therapy as described in U.S. Provisional Application No. 62/331,060 incorporated herein by reference.

Connection transferring high frequency (above 100 kHz) signal between individual parts of the device (e.g. connecting of the applicator or other devices) may be provided by special magnetic connection transferring high frequency signal or high frequency signal and data.

Such magnetic connection may be easier, faster way how to connect high frequency source and may have longer durability than connector based on principal sinking or latching one part of connector to another part of connector.

Figure 9A:
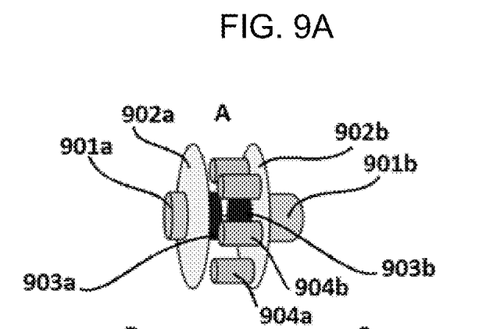
Figures 9B, 9C:
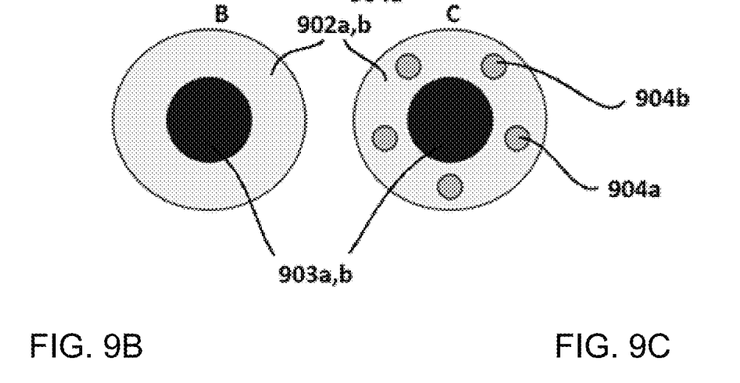

One of possible embodiment of such connection is illustrated in the FIGS. 9 A, B and C. FIG. 9 A illustrates both parts of the connector connecting together a lower part and an upper part of the connector, which are shown in FIGS. 9B and 9C respectively.

The connector includes supply cables 901a and 901b attached to conductive plates 902a and 902b. The upper and/or the lower part of the connector is attached to permanent or temporary magnet(s) 903a, 903b in order to provide connection between both parts. High frequency signals may be transferred between the lower and the upper connector part by a conductive connecting member(s) 904a and 904b rising from the lower and/or the upper part of the connector.

Conductive plates 902a and 902b may be replaced by more conductive elements located in the lower and the upper part of the connector.

The number, size and shape of the conductive connecting members 90 may vary. The connecting members 904 may be formed as pins or cylinders as shown in FIGS. 9A and 9C.

The diameter of the cylinder may be in range 0.1 mm to 5 cm or 0.1 mm to 1 cm or in range 0.1 mm to 5 mm. The cylinders may be replaced by a conductive ring, The cylinders may have at least partial spherical objects on one end and/or be provided with other shapes of conductive connecting members 904. Conductive connecting member(s) 904 is connected with supply cable(s) 901 by conductive plate(s) 901, directly or through other conductive or semi-conductive members. When the connector is connected, at least one conductive connecting member 904 is in contact with both parts of the connector. Conductive connecting member 904 may be made from conductive or semi-conductive material(s).

High frequency signals are mostly transferred on the surface of the conductive connecting member 904. To minimize overheating the magnet(s) 903, and to minimize inducting of electric or electromagnetic fields acting against transferred high frequency signals in conductive connecting member(s) 904, the conductive connecting members 904 are placed around the central magnet(s) 903 as shown in FIGS. 9A-9C. The high frequency connector may also be used as a coaxial cable.

Thus, various embodiments have been shown and described. Changes and substitutions may of course be made without departing from the spirit and scope of the invention. The invention, therefore, should not be limited, except by the following claims, and their equivalents.

The invention claimed is:

1. A method of soft tissue treatment of a patient comprising:
    placing an applicator onto a surface of the soft tissue, with the applicator including an electrode, a dielectric material vacuum cup and a dielectric material located under the electrode, with the dielectric material vacuum cup having a stiffness in a range from shore A5 to shore A80;
    providing radiofrequency energy from the electrode in a frequency range between 0.5 MHz to 100 MHz; and
    heating the soft tissue via the radiofrequency energy while applying vacuum to the vacuum cup.

2. The method of claim 1 wherein the vacuum is applied in pulses in a range from 0.5 kPa to 20 kPa.

3. The method of claim 2 with the dielectric material located under the electrode having thickness T1, and with T1 at least 5% thicker than the dielectric material below a center of the electrode.

4. The method of claim 3 wherein the dielectric material vacuum cup and the dielectric material under the electrode comprise a single part.

5. The method of claim 3 further including placing a second applicator onto a second surface of the soft tissue, with the second applicator including a second electrode and a second dielectric material vacuum cup.

6. The method of claim 5 with the heating further including using capacitive heating by the two or more applicators and applying energy to the soft tissue from another treatment energy source.

7. The method of claim 2 wherein the dielectric material under the electrode has a thermal conductivity in a range 0.05 to 1 $Wm^{-1} \cdot K^{-1}$.

8. The method of claim 7 wherein the dielectric material under the electrode has a dielectric constant in a range 1.5 to 12.5.

9. The method of claim 8 wherein the dielectric material under the electrode has a thickness in a range from 0.2 mm to 12 cm.

10. The method of claim 2 including using a control unit for regulating the vacuum applied to the vacuum cup.

11. The method of claim 2 wherein one or more of the pulses has a duration in a range between 0.1 s to 100 s.

12. The method of claim 11 including changing a contact area between the dielectric material under the electrode and the patient's soft tissue surface.

13. The method of claim 1 further including providing a temperature difference $\Delta T_1$ between a contact part of the applicator and an adipose tissue with $\Delta T_1$ in a range between 0-18° C.

14. The method of claim 13 further including providing a temperature difference $\Delta T_2$ between the patient's epidermis and the adipose tissue with $\Delta T_2$ in a range between 0-18° C.

15. The method of claim 14 further including using a temperature control system to regulate at least one of $\Delta T_1$ or $\Delta T_2$.

16. The method of claim 13 with the heating further including capacitive heating by the electrode of the adipose tissue to a temperature in a range between 41-48° C.

17. The method of claim 1 further including providing a high frequency signal to the electrode through a connector including a conductive connecting member placed around a central magnet.

18. The method of claim 1 further including controlling the radio frequency signal to the electrode using a high frequency generator, a balun transformer, an impedance matching circuit, and a control unit; and further controlling the vacuum in the vacuum cup by a pump and the control unit.

19. A method of soft tissue treatment of a patient comprising:
    placing an applicator onto a surface of the soft tissue, with the applicator including an electrode and a dielectric material vacuum cup;
    with a dielectric material covering at least part of the electrode;
    wherein the dielectric material covering at least part of the electrode has a thickness T1 below an edge of the electrode and T2 below a center of the electrode, while T1 is at least 5% thicker than T2;
    applying vacuum to the vacuum cup; and
    heating the soft tissue via the electrode.

20. The method according to claim 19 including heating the soft tissue in a sequence according to a temperature profile with a sequentially repeated temperature rise of at least 0.2° C. and temperature decrease of at least 0.2° C. until a predefined soft tissue temperature is reached.

21. The method according to claim 19 further including providing massage by repeatedly changing a pressure value under the applicator.

22. The method according to claim 21 further including creating temperature difference $\Delta T_3$ between epidermis and non-adipose tissue in dermis in range between 0-18° C.

23. The method according to claim 19 further including providing vacuum under the applicator around the electrode and through the dielectric material located under the electrode or through the dielectric material vacuum cup.

24. The method according to claim 23 further including providing treatment by an even number of applicators with one electrode exhibiting bipolar behavior.

25. The method according to claim 19 wherein surface size of the electrode is in a range from 1 $cm^2$ to 1200 $cm^2$.

26. A method of soft tissue treatment of a patient comprising:
    placing an applicator onto a surface of the soft tissue, with the applicator including an electrode on top of a dielectric material vacuum cup and a dielectric material located under the electrode;
    the electrode providing radio frequency treatment in a frequency range between 0.5 MHz to 100 MHz;
    applying a pulsating negative pressure to the vacuum cup, wherein the negative pressure is applied in pulses in a range from 0.5 kPa to 20 kPa, with a duration of one or more of the pulses in a range between 0.1 s to 100 s; and
    simultaneously heating the soft tissue.

27. A method of soft tissue treatment of a patient comprising:
    placing at least two applicators onto a surface of the soft tissue, with each applicator including one electrode on top of a dielectric material vacuum cup and a dielectric material located under the electrode;
    each electrode providing radio frequency treatment in a frequency range between 0.5 MHz to 100 MHz;
    applying a negative pressure to each vacuum cup;
    controlling the electrodes of the at least two applicators by using a high frequency generator, a balun transformer, an impedance matching circuit and a control unit;
    controlling the negative pressure in the vacuum cups by a pump and the control unit;
    changing a contact area of the dielectric material located under the electrode with the patient's soft tissue surface by the application of the negative pressure pulses; and
    simultaneously capacitively heating the soft tissue between the applicators.

* * * * *